United States Patent
McCrary et al.

(10) Patent No.: US 7,601,001 B1
(45) Date of Patent: Oct. 13, 2009

(54) SUCTION APPARATUS HOLDER

(75) Inventors: Craig R. McCrary, Valencia, CA (US); Arnold M. Heyman, Los Angeles, CA (US); Thomas R. Thornbury, Los Angeles, CA (US)

(73) Assignee: Neotech Products, Inc., Valencia, CA (US)

( * ) Notice: Subject to any disclaimer, the term of this patent is extended or adjusted under 35 U.S.C. 154(b) by 713 days.

(21) Appl. No.: 11/185,520

(22) Filed: Jul. 21, 2005

(51) Int. Cl.
*A61C 13/38* (2006.01)
*A61G 15/00* (2006.01)
*A47F 5/00* (2006.01)
*B65D 83/10* (2006.01)

(52) U.S. Cl. ................. 433/77; 206/363; 248/309.1
(58) Field of Classification Search .............. 206/570, 206/571, 363–365, 210, 438; 248/309.1, 248/314, 176.1; 433/77–79; 211/70.6, 85.13, 211/60.1
See application file for complete search history.

(56) References Cited

U.S. PATENT DOCUMENTS

| | | | |
|---|---|---|---|
| 1,904,510 A * | 4/1933 | Mott .................. 135/34.2 |
| 3,630,385 A * | 12/1971 | Searcy .................. 211/70.6 |
| 4,852,844 A * | 8/1989 | Villaveces .................. 248/314 |
| 5,370,627 A | 12/1994 | Conway |
| 5,584,403 A * | 12/1996 | Sipperly .................. 211/63 |
| 5,727,701 A * | 3/1998 | Rhoades .................. 211/70.6 |
| 5,743,394 A * | 4/1998 | Martin .................. 206/378 |
| 5,743,415 A * | 4/1998 | Smart .................. 211/70.6 |
| 5,752,286 A | 5/1998 | Wright |
| 5,806,822 A * | 9/1998 | Schulz .................. 248/309.1 |
| 5,927,974 A * | 7/1999 | Homra .................. 433/77 |
| 6,689,104 B2 * | 2/2004 | Bierman .................. 604/174 |
| 7,377,780 B2 * | 5/2008 | White et al. .................. 433/77 |
| 2005/0194507 A1 * | 9/2005 | White .................. 248/314 |

* cited by examiner

*Primary Examiner*—Mickey Yu
*Assistant Examiner*—Melissa L Lalli
(74) *Attorney, Agent, or Firm*—William W. Haefliger

(57) ABSTRACT

Apparatus for storing a suctioner and the end of a suction line after disconnection from the suctioner, comprising support means, first storage structure on the support means for storing the suctioner; and second storage structure on the support means for storing the end of the suction line and for blocking suction flow of air into the line via the end.

5 Claims, 3 Drawing Sheets

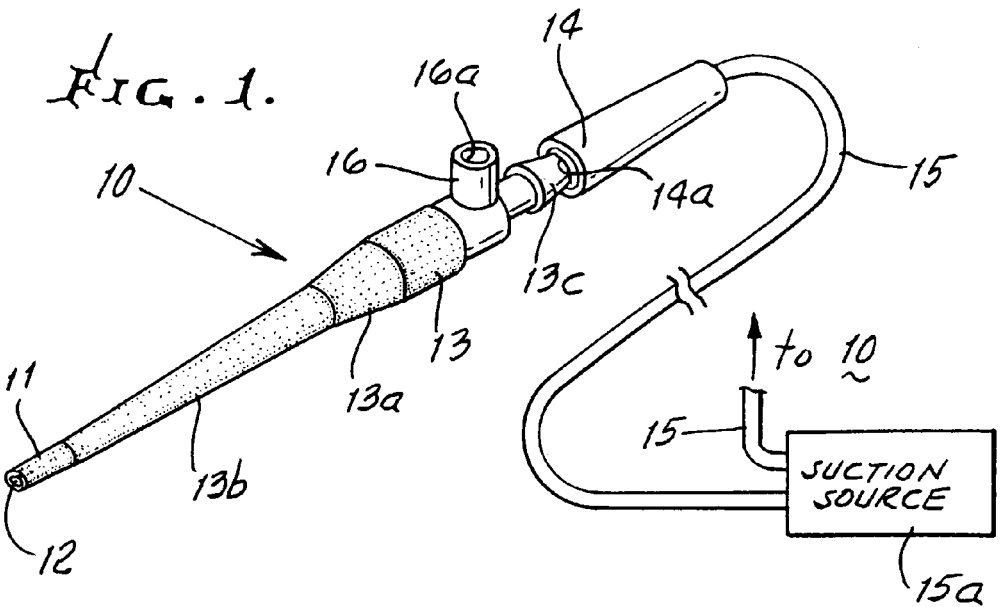
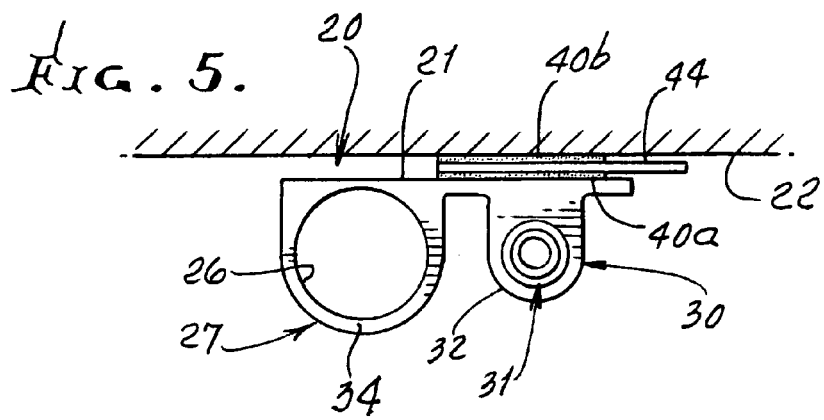
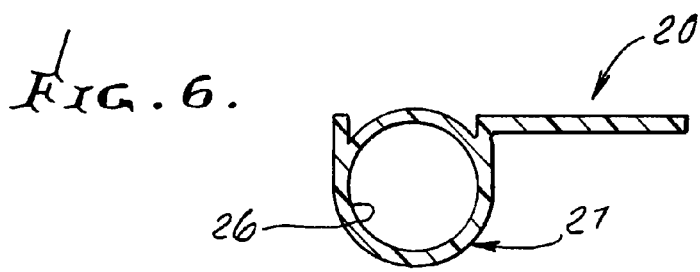

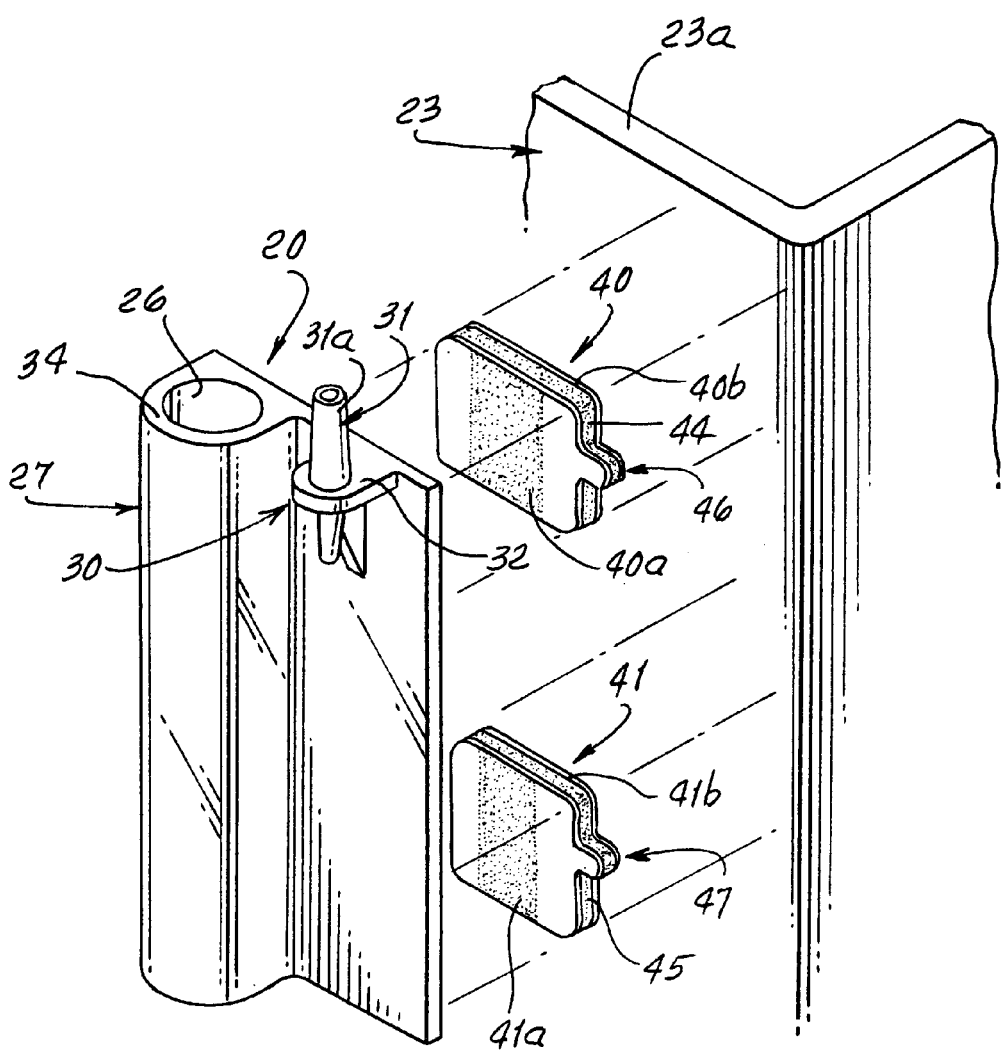

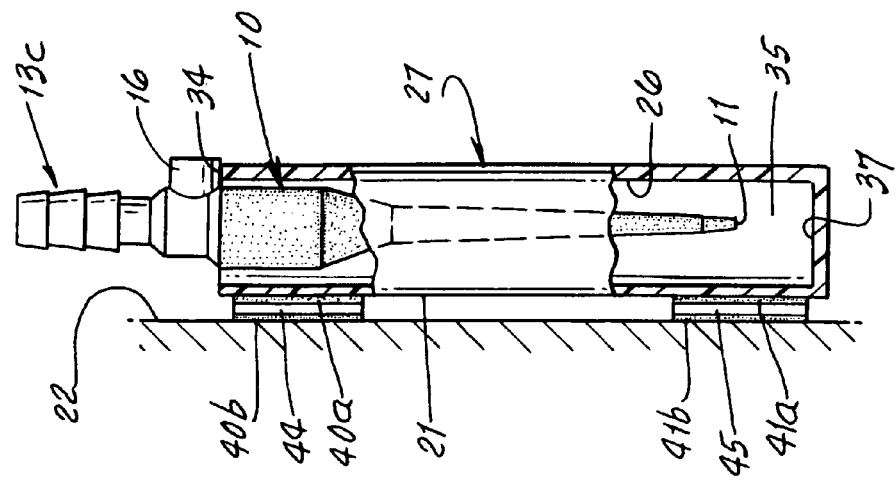
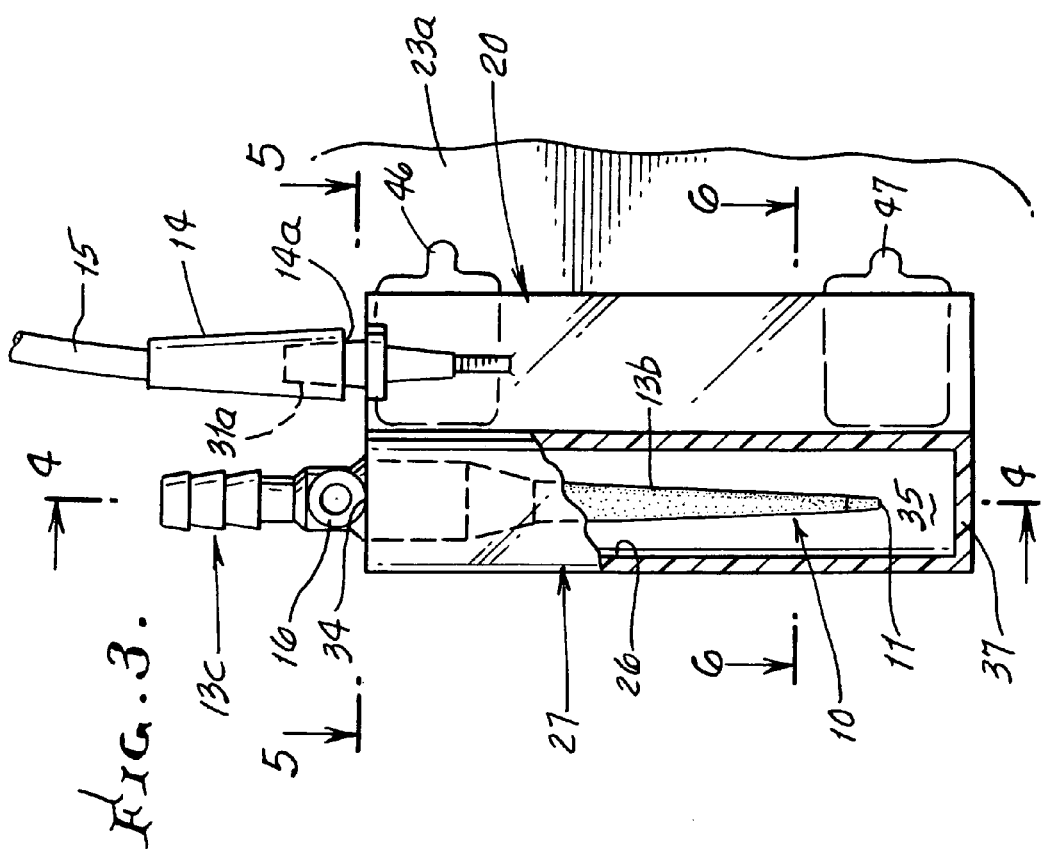

SUCTION APPARATUS HOLDER

BACKGROUND OF THE INVENTION

This invention relates generally to use by medical technicians of suctioning devices, as in hospitals, and more particularly concerns elimination of suctioning noise during interrupted periods of use of such devices.

Suctioning apparatus is commonly used as for example to remove oral or nasal secretions from infants after birth, and to remove other unwanted fluids encountered during medical procedures.

During periods of temporary non-use, the devices are usually set to one side, as on a table, bed, or bassinet; however, there is need to temporarily store such devices for ready use. Also, there is need to eliminate disturbing suctioning noise produced by the device as during such temporary storage.

BACKGROUND OF THE INVENTION

It is a major object of the invention to provide means to meet the above needs, in an efficient, easily usable manner. Basically, a major object is to provide apparatus for storing a suctioner and the end of a suction line after disconnection from the suctioner, comprising in combination:

a) support means, b) first storage structure on the support means for storing the suctioner; and c) second storage structure on the support means for storing said end of the suction line and for blocking suction flow of air into said line via said end.

Another object is to provide the support means in the form of a base on which both storage structures are carried, in mutual proximity. As will be seen, the first storage structure typically comprises an upwardly opening receptacle to receive the suctioner; and the second support structure comprises a plug to fit the end of the suction line and block production of suction noise.

Another object is to provide a securing mechanism on the base to enable its quick attachment to an upright wall proximate the location of suctioning use.

Yet another object is to provide, in combination:

a) a group of bassinets, for infants, each bassinet having an upright wall, b) a base, first and second storage structure on the base, and means for attaching the base to one of the walls, c) the first storage structure providing a receptacle to receive a suctioning device; and the second storage structure providing means to block the end of a suctioning line or duct.

These and other objects and advantages of the invention, as well as the details of an illustrative embodiment, will be more fully understood from the following specification and drawings, in which:

DRAWING DESCRIPTION

FIG. 1 is a perspective view of suctioning apparatus, including a suction line removably attached to a suction producing device;

FIG. 2 is a perspective view of a storage means for the elements shown in FIG. 1, when disassembled, together with means to connect the storage means to a wall, as for example a bassinet wall;

FIG. 3 is a vertical elevation showing interior construction of preferred storage means;

FIG. 4 is a vertical section taken on lines 4-4 of FIG. 3; and

FIGS. 5 and 6 are horizontal sections taken on lines 5-5 and 6-6 respectively of FIG. 3.

DRAWING DESCRIPTION

In FIG. 1 a suctioner 10 has a narrow elongated tip 11 defining an entrance 12 for fluid being suctioned, as for example infant fluid such as oral or nasal secretions. The suctioner tubular body 13 tapers at 13a toward elongated extent 13b from which tip 11 projects. Body 13 has reduced diameter tubular portion 13c to which a suctioning tube end 14 is removably endwise telescopically connected or is connectible, as by push-on assembly. Tube end 14 is in turn connected via a flexible suction tube or line 15 to a suction source 15a. A short side or stub tube 16 on body 13 communicates with the interior of the body 13, and is controllable as by application of the user's finger to the side tube inlet 16a, to control the degree of suction application to the entrance 12, as by aspiration action. Various forms of elongated suctioners may be provided, the FIG. 1 suctioner being only one of such forms.

After use of the suctioner 10 and after disconnection of the suction tube end 14 from the suctioner tubular portion 13c, there are three needs, as follows:

i) need to store the suctioner 10;

ii) need to store the removed suction tube end 14 near the suctioner for re-assembly and use, iii) need to eliminate the harsh suction produced noise, of air being sucked into the inlet opening 12 at the end of the tube 14.

FIGS. 2-5 illustrate a simple, efficient, easily used and mounted preferred means to meet the above three needs. As shown, a support means is provided, as for example in the form of a base 20 which may have a mounting surface 21 to face and connect or adhere to a wall 22, such as the upright side wall 23a of an infant's bassinet 23.

A first storage structure is provided on the support means, or base 20, for storing the suctioner 10. That structure preferably comprises a holder or receiver for the suctioner to hold the suctioner in stored condition. The illustrated and preferred receiver comprises an upright receptacle or bore 26 in upright body 27, attached to or integral with the base and which opens upwardly, as shown. The bore 26 may form a well to receive disinfecting liquid.

A second storage structure is also provided on or integral with the support means or base, for storing the tubular end 14 of the suction line, and for blocking suction flow of air into tube end 14 and into the suction line 15. That structure is generally designated at 30, and includes an upright plug 31 carried by a sidewardly projecting flange 32 integral with the base. When the open inlet 14a of the tube end 14 is placed downwardly on and over the plug, that end becomes plugged or closed so that air cannot be suctioned into tube end 14, thereby shutting off the harsh suctioning sound of air being sucked into end 14, and enabling remote suction source 15a to remain "ON". Also, the plug may have an upwardly tapering wall 31a to closely fit the inlet 14a as the tube end 14 is placed downwardly on the plug. Flange 32 may provide additional upper surface support for the tube end 14, or structure mounted with that end. Finally, since the plug is close to the receptable 26, the tube end 14 can be quickly lifted off the upright plug and telescopically fitted endwise to the suctioner, as referred to above. FIG. 3 shows the upwardly presented or protruding tubular portion 13c of the stored suctioner to which tube end 14 is easily and quickly connectible. Note that stub tube 16 may engage a receptacle shoulder 34 (see FIG. 4) allowing the narrowed inlet tip 11 to be protectively spaced at 35 from the bottom wall 37 of the elongated receptacle, preventing damage to that stored tip. The shoulder may be U-shaped, i.e. upwardly concave to receive the tube 16 lower extent, for secure retention.

FIGS. 2 and 5 show the provision of attachment means for removably attaching the base 20 to the wall 22 of a bassinet. Note the provision of two (upper and lower) patches 40 and 41, adherent at 40a and 41a to the surface of the base, and adherent at 40b and 41b to the bassinet wall. This allows hospital personnel to quickly attach the unitary storage structure described above to an infant's bassinet, or other associated structures, at the locus of use of the suctioner; and a group of such storage structures may be provided at each of a series of bassinets, in a hospital room where newborn infants are received, for efficient, individual suctioning use, and connection to a suction source.

Carriers for the adhesive layers 40a, 40b, 41a and 41b are shown at 44 and 45, and tab handles to aid manipulation are shown at 46 and 47. Typically the adhesive patches are affixed to the base 20, to allow positioning of the storage apparatus relative to wall 22 or wall 23a.

The receptacle 27, plug 31, base 20 and associated structure may consist of molded plastic material.

Alternate attachment means may include suction cups, hooks, or clips.

We claim:

1. Apparatus for storing a suctioner and an end of a suction line after disconnection from the suctioner, comprising in combination with said suctioner and said suction line having said end, a) a support means, b) a first storage structure on the support means storing said suctioner including a downwardly elongated receptacle receiving said suctioner in an upright position, the receptacle opening upwardly; and c) a second storage structure on the support means storing said end of said suction line and blocking suction flow of air into said suction line via said end, d) said support means comprising a base on which both storage structures are carried, in mutual proximity, e) said suctioner having a side inlet defined by a stub tube, engaging a shoulder defined by said first storage structure to limit downward reception of said suctioner into said first storage structure f) said shoulder configured to stabilize the positioning of the stub tube, and upright positioning of said suctioner in the receptacle.

2. The combination of claim 1 wherein said shoulder is upwardly concave to nest the stub tube with enhanced stabilization.

3. The combination of claim 1 wherein said second storage structure comprises a plug to fit said end.

4. The combination of claim 1 including a means on the base for attaching the base to an upright wall.

5. The combination of claim 4 wherein said means on the base for attaching the base to an upright wall comprise at least one adhesive pad affixed to the base, having a projecting tab for manipulation.

* * * * *